United States Patent
Pryce et al.

(10) Patent No.: US 6,409,887 B1
(45) Date of Patent: Jun. 25, 2002

(54) POLYMERIZATION INHIBITOR

(75) Inventors: Anthony Pryce, Leeds; Robert Charles Callin, Ben Rhydding, both of (GB)

(73) Assignee: AAH Marks and Company Limited, Wyke Bradford (GB)

( * ) Notice: Subject to any disclaimer, the term of this patent is extended or adjusted under 35 U.S.C. 154(b) by 1 day.

(21) Appl. No.: 09/834,328

(22) Filed: Apr. 13, 2001

Related U.S. Application Data

(63) Continuation of application No. 09/230,013, filed as application No. PCT/GB97/01908 on Jul. 15, 1997, now abandoned.

(30) Foreign Application Priority Data

Jul. 15, 1996 (GB) .............................................. 9614854

(51) Int. Cl.⁷ .............................. C07C 7/05; C07C 7/00
(52) U.S. Cl. ....................... 203/9; 585/2; 585/3; 585/4; 585/5; 585/950; 208/48 AA; 203/8
(58) Field of Search ................................ 585/2, 3, 4, 5, 585/950; 208/48 AA; 203/8, 9

(56) References Cited

U.S. PATENT DOCUMENTS

| | | | |
|---|---|---|---|
| 3,163,677 A | * 12/1964 | Hoffman et al. ............. 564/310 |
| 3,334,103 A | * 8/1967 | Feldman et al. ............. 546/249 |
| 3,502,692 A | * 3/1970 | Feldman et al. ............. 548/531 |
| 5,254,760 A | 10/1993 | Winter ........................... 585/5 |
| 5,488,192 A | 1/1996 | Kourbatov et al. .......... 585/435 |
| 5,545,782 A | 8/1996 | Winter et al. ................... 585/5 |
| 5,545,786 A | 8/1996 | Winter et al. ............... 585/435 |
| 5,728,872 A | 3/1998 | Riemenschneider ........ 562/598 |
| 5,744,672 A | 4/1998 | Kourbatov et al. .......... 585/440 |
| 5,907,071 A | 5/1999 | Arhancet ........................ 585/5 |
| 5,910,232 A | 6/1999 | Hyde et al. ..................... 203/9 |

FOREIGN PATENT DOCUMENTS

| | | |
|---|---|---|
| EP | 0 550 754 | 7/1993 |
| EP | 0 697 386 | 2/1996 |
| SU | 819078 | 4/1981 |
| WO | 95/03263 | 2/1995 |

* cited by examiner

*Primary Examiner*—Walter D. Griffin
(74) *Attorney, Agent, or Firm*—Darby & Darby

(57) ABSTRACT

A monomer composition, stabilized against premature polymerization, comprising: a) an ethylenically unsaturated monomer or mixture of monomers polymerizable by free radical initiation, and b) an effective amount, sufficient to inhibit premature polymerization of component (a) of a mixture of: i) 1 to 99% by weight, based on the total weight of components (i) and (ii), of a mixture of at least one aromatic amine and at least one organic acid in a molar ratio of 10:1 to 1:10, and ii) 99 to 1% by weight, based on the total weight of components (i) and (ii), of at least one stable radical compound.

7 Claims, No Drawings

POLYMERIZATION INHIBITOR

This is a continuation of application Ser. No. 09/230,013, filed Jan. 14, 1999, now abanodoned, which is a 371 of PCT Application No. PCT/GB97/0198, filed Jul. 15, 1997, and claims the benefit of Great Britain Application No. 9614854.9 filed Jul. 15, 1996. Each of these prior applications is hereby incorporated herein by reference, in their entirety.

FIELD OF THE INVENTION

This invention relates to free radical scavengers for use as or in connection with inhibitors of olefinic polymerisation, particularly but not exclusively for inhibition of polymerisation of vinyl aromatic compounds.

BACKGROUND OF THE INVENTION

Olefinic compounds such as butadiene, acrylic monomers, styrene and other vinyl aromatic compounds have a strong tendency to polymerise on storage or heating. High temperature techniques such as distillation are commonly used during separation and purification processes and the industrial production of these olefinic compounds.

Although free radical scavengers have been used to prevent olefinic polymerisation, there is a requirement for higher efficiency scavengers which may be used at lower concentrations or for scavengers which are more efficient at the same concentrations as are currently employed. Lower concentrations are economic, less toxic and are environmentally beneficial. More efficient compositions are economic, giving reduced wastage and/or prolongation of the active life of the olefin.

Various compounds and compositions have been used as free radical scavengers to prevent or reduce undesired polymerisation of olefinic compounds during high temperature processes. These inhibitors have given varying degrees of success. In a typical process an olefinic compound may be contacted with the inhibitor before distillation or other processing. However the amount of polymer formed during such processing may be substantially higher than desired, leading to economic loss. In other cases it may be possible to achieve economically desirable low levels of polymerisation but only by use of economically unacceptable quantities of the inhibitor. Sulphur has been widely employed as a polymerisation inhibitor but difficulties in handling and disposal have lead to replacement by non-sulphur inhibitors, referred to as NSIs. SU-A-819078 discloses use of 3,5-ditertiary butyl-4-oxy-N,N-dimethylbenzylamine in combination with a $C_{10}$–$C_{20}$ aliphatic carboxylic acid. However the concentrations of this particular NSI are sufficiently large (500 to 2200 ppm) that much of the NSI is not consumed in a typical process. This results in uneconomic quantities of residual NSI being present in the effluent or waste from the process. EP-A-550754 discloses a polymerisation inhibitor for vinyl compounds combining a reaction product of 4-(dimethylamino)methyl-2,6-bis(tert butyl)phenol with an inorganic or carboxylic acid in the weight ratio 1 to 15:3. WO95/03263 discloses reduction in the quantity of this NSI by use in combination with air. However it is undesirable to introduce air into many high temperature processes involving olefinic compounds. Firstly there is an economic cost associated with ensuring a supply of the required quantity of air. Secondly it is often a safety hazard to introduce air into the stream of a hot olefinic compound due to the risk of oxidation, fire or an explosion.

Use of stable free radicals for inhibiting polymerisation by scavenging other free radicals has been disclosed. G M Burnett, Mechanism of Polymer Reactions, Interscience, New York 1954, 76, stated that a sterically hindered nitroxyl radical, 2,2,6,6-tetramethyl piperidinyl-1-oxyl (referred to as TEMPO) is effective against carbon centred radicals. Use of stable free radicals as scavengers was reviewed by E G Rozantsev, Free Nitroxyl Radicals, Plenan Press, 1970, 105. The practical utility of nitroxyl radicals as scavengers to prevent polymerisation was disclosed in GB 1127127 and GB 1218456. The high cost of stable free radicals has restricted their commercial use and there remains a requirement for an economic means of preventing or controlling polymerisation. U.S. Pat. No. 4,670,131 disclosed that certain stable free radicals may be used as polymerisation inhibitors under certain conditions at levels less than 700 parts per billion. However such low usage rates are not of general applicability.

SUMMARY OF THE INVENTION

We have now found that a free radical scavenger composition including an aromatic amine in combination with an organic acid and a stable free radical compound is effective without the economic disadvantages of the previously disclosed compositions.

According to a first aspect of the present invention a monomer composition, stabilised against premature polymerisation, comprises:

a) an ethylenically unsaturated monomer or mixture of monomers polymerisable by free radical initiation, and b) an effective amount, sufficient to inhibit premature polymerisation of component (a) of a mixture of;
  i) 1 to 99% by weight, based on the total weight of components (i) and (ii) of a mixture of at least one aromatic amine and at least one organic acid in a molar ratio of 10:1 to 1:10, and
  ii) 99 to 1% by weight based on the total weight of components (i) and (ii) of at least one stable radical compound.

Compositions in accordance with this invention exhibit a synergistic effect in that the inhibition efficiency is greater than that of the two components. Preferred monomers are vinyl aromatic compounds for example styrene, methyl styrene, vinyl toluene or divinyl benzene or vinyl aliphatic compounds including acrylonitrile, acrylic acid, methacrylic acid, acrylate esters, methacrylate esters, butadiene and butenes. The invention is particularly applicable in inhibition of polymerisation of styrene during distillation, purification or storage.

DETAILED DESCRIPTION OF THE INVENTION

In preferred compositions the weight of component i) is 50 to 99% and the weight of component ii) is 50 to 1%. In particularly preferred embodiments of the invention the weight of component i) is 67 to 99% and the weight of component ii) is 33 to 1%.

Percentages and other amounts in this specification are by weight unless indicated otherwise. Percentages and other proportions are selected to total 100%.

The molar ratio of said at least one aromatic amine to said at least one organic acid is 3:1 to 1:3.

In preferred embodiments of the invention the aromatic amine has the formula (1)

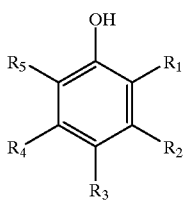

(1)

wherein Q is O or S or N-Z and wherein at least one R is an alkyl amine of the structure (2)

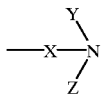

(2)

in which Y, Z are the same or different and comprise $C_1$ to $C_4$ branched or straight chain alkyl or hydrogen and in which X is either a covalent bond or $C_1$ to $C_4$ alkylene, and wherein each remaining R is independently benzyl, $C_1$ to $C_4$ branched or straight chain alkyl or hydrogen with the provision that two or more R may be connected to form one or more rings.

Q is preferably oxygen.

X is preferably methylene.

Y and Z are preferably methyl.

$R^1$ and $R^5$ are preferably tertiary butyl.

A preferred amine has Y and Z as methyl and $R^2$ and $R^4$ as hydrogen.

Preferred amines include benzylamine and benzylamine derivatives, for example 3,5-tertiarybutyl-4-hydroxybenzylamine, anilines and phenylene diamines, for example N,N-dimethyl-1,4-phenylenediamine 3,5-ditertiarybutyl-4-oxy, N,N-dimethylbenzylamine 3,5-ditertiarybutyl-4-oxy-N,N-diethylbenzylamine N,N-dimethyl-2,6-ditertiarybutyl-4-amino phenol 1,4-phenylenediamine N,N-dimethyl-4-aminothiophenol N,N'-bis-(1,4 dimethylpentyl)-1,4-phenylenediamine In preferred embodiments of the invention the organic acid is a carboxylic acid. $C_6$ to $C_{22}$, preferably $C_6$ to $C_{18}$ saturated or unsaturated carboxylic acids are particularly efficacious. These may be substituted with groups inert to attack by the nitroxyl radical. Linear or branched chain acids may be employed. Branch chain acids which are liquid at ambient temperatures are convenient to manipulate. Unsubstituted saturated acids are especially preferred.

The stable radical compound is preferably a sterically hindered nitroxyl of the formulae (3)

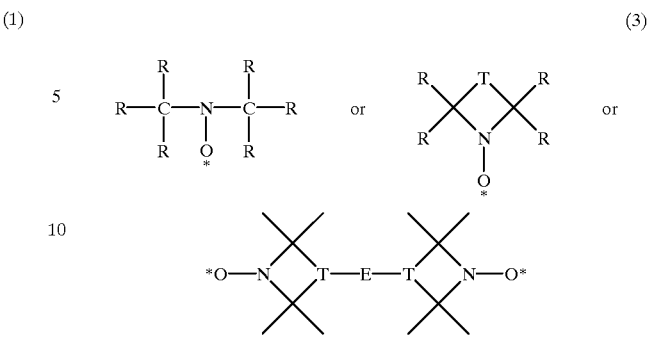

(3)

wherein R is hydrogen, alkyl or aryl and T is a group required to form a ring and wherein two or more T groups may be linked by a linking group E.

Preferred nitroxyl compounds may be selected from:

1-oxyl-2,2,6,6-tetramethylpiperidin, 1-oxyl-2,2,6,6-tetramethylpiperidin-4-ol, 1-oxyl-2,2,6,6-tetramethylpiperidin-4-one, 1-oxyl-2,2,6,6-tetramethylpiperidin-4-yl acetate, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethlpiperidin-4-yl benzoate, 1-oxyl-2,2,6,6-tetramethylpiperidin-4-yl 4-tert-butylbenzoate, bis(1-oxyl-2,2,6,6-tetramethylpiperidin-4-yl)succinate, bis(1-oxyl-2,2,6,6-tetramethylpiperidin-4-yl) sebacate, bis(1-oxyl-2,2,6,6-tetramethylpiperidin-4-yl) sebacate, bis(1-oxyl-2,2,6,6-tetramethylpiperidin-4-yl) adipate, bis(1-oxyl-2,2,6,6-tetramethylpiperidin-4-yl) n-butylmalonate, bis(1-oxyl-2,2,6,6-tetramethylpiperidin-4-yl)phthalate, bis(1-oxyl-2,2,6,6-tetramethylpiperidin-4-yl) isophthalate, bis(1-oxyl-2,2,6,6-tetramethylpiperidin-4-yl) terephthalate, bis(1-oxyl-2,2,6,6-tetramethylpiperidin-4-yl) hexahydoterephthalate, N,N'bis(1-oxyl-2,2,6,6-tetramethyulpiperidin-4-yl) adipamine, N-(1-oxyl-2,2,6,6-tetramethylpiperidin-4-yl) caprolactam, N-(1-oxyl-2,2,6,6-tetramethylpiperidin-4-yl) dodecylsuccinimide 2,4,6-tris-[N-butyl-N-(1-oxyl-2,2,6,6-tetramethylpiperidin-4-yl]-s-triazine, and 4,4'-ethylenebis(1-oxyl-2,2,6,6-tetramethylpiperidin-3-one)

4-acetylamino 2,2,6,6-tetramethylpiperidin-N-oxyl

Most preferably, the compound of component b) is 1-oxyl-2,2,6,6-tetramethylpiperidin-4-ol, or bis(1-oxyl-2,2,6,6-tetramethylpiperidin-4-yl) sebacate Preferred nitroxyl compounds are piperidinoxyl compounds.

According to a second aspect of the present invention a process for inhibiting premature polymerisation of a vinyl aromatic or aliphatic compound during distillation, purification or storage, comprises the step of incorporating therein an effective inhibiting amount, sufficient to prevent premature polymerisation during distillation, purification or storage of a mixture of i) 1 to 99% by weight, based on the total weight of components (i) and (ii), of an admixture of at least one aromatic amine and at least on organic acid in a molar ratio of from 10:1 to 1:10 and ii) 99 to 1% by weight, based on the total weight of components (i) and (ii), of at least one stable radical compound.

Preferred processes of this invention use a stabilising composition which is synergistic in nature, that is using half the concentration of component a) together with half the concentration of component b) to afford a greater stabilisation efficacy than may be achieved using either component a) or b) alone.

Preferred processes in accordance with this invention employ stabilising compositions as described above with reference to the first aspect of this invention.

The effective amount of polymerisation inhibitors employed may vary over a wide range depending upon the particular olefinic compound and the distillation or other purification conditions employed. Preferably the total amount of an aromatic amine and an aliphatic carboxylic acid and a stable free radical is from 1 ppm to 2000 ppm based upon the weight of the olefinic compound. For most olefinic compounds the mixture of components a) and b) is 5 to 1000 ppm. Greater amounts of inhibitor are required at higher temperatures. During distillation of olefinic mixtures the temperature of the reboiler may be up to about 150° C. Since the boiling points of the various aromatic amines of component a) and of the various stable free radicals b) are different, compounds which have the desired boiling points can be easily selected. The compositions of this invention which inhibit the polymerisation of the olefinic compound are also well suited for protecting the re-boiler sections of a distillation column or the compressor sections before entering a distillation column.

The polymerisation inhibitor can be introduced into the olefinic compound to be protected by any conventional method. It may be added as a concentrated solution in a suitable solvent. Since the solubilities of the various aromatic amines of component a) of the various organic acids of component a) and of the various stable free radicals of component b) are different, compounds which have the desired solubilities can be easily selected. The components a) and b) may be injected separately into the distillation train along with the incoming feed, or through separate entry points providing there is an efficient distribution of the inhibitors.

The inhibitors are gradually depleted during the distillation operation. Consequently it is generally necessary to maintain the appropriate amount of inhibitor mixture in the distillation apparatus by adding inhibitors during the course of the distillation process. Such addition may be carried out either on a generally continuous basis or it may consist of intermittently charging inhibitor into the distillation system in order to maintain the concentration of the inhibitor in excess of the minimum required level. The amine and carboxylic acid may be added separately at different entry points into the process stream.

The present invention enables the distillation and purification of olefinic compounds in manufacturing plants to operate more economically compared to prior art processes because of the greater effectiveness with or without the presence of oxygen. This permits lower inhibitor usages with minimal polymer formation.

The present invention also enables the storage of olefinic compounds for prolonged periods of time at ambient or elevated temperatures with or without the presence of oxygen by utilising economically beneficial amounts of the scavenger composition to minimise polymer formation.

The present invention is further described by means of example but not in any limitative sense.

EXAMPLES 1 to 3

Commercial quality styrene was washed with dilute caustic soda solution to remove the storage stabiliser, tert-butylcatechol. The styrene was then washed with water to remove excess alkali, following which it was dried over anhydrous sodium sulphate prior to use as follows;

Inhibitor and styrene (enough to make total weight of mixture of 200 g) were charged to a 250 ml round-bottomed flask fitted with an overhead stirrer, thermometer, sparge tube and water cooled condenser (see diagram below). The stirrer was started. Nitrogen (200 ml min$^{-1}$) sparging through the reaction mixture was then applied. The reaction mixture was then heated to 100° C. using an oil bath, and stirred at this temperature for two hours. Samples were removed and analysed for polystyrene content using a spectrophotometric method at 420 nm. The analysis method was based on American Standard Test Method D2121 and a calibration was made using authentic polystyrene in styrene solutions of known concentrations by weight. In a controlled experiment, without any inhibitor present much greater than 30000 ppm (limit of quantification) of polystyrene was formed. Polymer levels obtained with various inhibitors present are shown in the table below. The blends of inhibitors were considerably more effective at reducing the amount of polymer formed than were either of the components when used individually at the full rate of inhibitor concentration. This clearly demonstrates that an unexpected synergistic effect occurs in the polymerisation inhibition of styrene in the absence or air by using both an aromatic amine-aliphatic carboxylic acid inhibitor and a stable free radical inhibitor together as compared to using either inhibitor alone at twice its concentration found in the combination.

| Example No | Inhibitors | ppm | Polymer (ppm) |
| --- | --- | --- | --- |
| Control | None | — | >30,000 |
| 1 | A | 33 | 23 448 |
| 2 | B | 517 | 754 |
| 3 | A plus B | 17 plus 258 | 50 |

A is 4-hydroxy-2,2,6,6-tetramethyl-piperidinyl-1-oxyl radical.
B is 3,5-ditertiarybutyl-4-oxy, N,N-dimethylbenzylamine in combination with stearic acid (molar ratio 1:1.5).

EXAMPLES 4 to 6

The procedure of Examples 1 to 3 was repeated with a higher test temperature of 115° C. and instead of a nitrogen sparge there was applied an air sparge (4 ml min$^{-1}$). The results of these tests are shown below;

| Example No | Inhibitors | ppm | Polymer (ppm) |
| --- | --- | --- | --- |
| 4 | A | 33 | 28 000 |
| 5 | B | 517 | 3 000 |
| 6 | A plus B | 17 plus 258 | 1 684 |

A is 4-hydroxy-2,2,6,6-tetramethyl-piperidinyl-1-oxyl radical
B is 3,5-ditertiary butyl-4-oxy-N,N-dimethylbenzylamine in combination with stearic acid (molar ratio 1:1.5).

There is a clear synergistic inhibiting effect on the polymerisation of styrene in the presence of air. When a mixture of the two inhibitor compounds are used together as compared to using either inhibitor alone at twice its concentration used in the combination.

EXAMPLES 7 to 9

The procedure of Examples 1 to 3 was repeated and instead of nitrogen sparge there was applied an air sparge (4 ml min$^{-1}$).

| Example No | Inhibitors | ppm | Polymer (ppm) |
|---|---|---|---|
| 7 | A | 10 | 14 |
| 8 | C | 150 | 18,230 |
| 9 | A plus C | 5 plus 75 | 0 |

A as 4-hydroxy-2,2,6,6-tetramethyl-piperidinyl-1-oxy radical
C is 3,5-ditertiary butyl-4-oxy N,N-dimethylbenzylamine in combination with stearic acid (molar ratio 1:3)

EXAMPLES 10 to 12

The procedure of Examples 7 to 9 was repeated but the time at 100° C. was 1 hour instead of 2 hours.

| Example No | Inhibitors | ppm | Polymer (ppm) |
|---|---|---|---|
| 10 | A | 2 | 1,562 |
| 11 | D | 30 | 1,684 |
| 12 | A plus D | 1 plus 15 | 49 |

A is 4-hydroxy-2,2,6,6-tetramethyl-piperidinyl-1-oxy radical
D is 1,4-phenylenediamine in combination with stearic acid (molar ratio 1:1.5)

EXAMPLES 13 to 15

The procedure of Examples 4 to 6 was repeated but the time at 115° C. was 1 hour instead of 2 hours.

| Example No | Inhibitors | ppm | Polymer (ppm) |
|---|---|---|---|
| 13 | A | 10 | 23,274 |
| 14 | E | 150 | 101 |
| 15 | A plus E | 5 plus 75 | 0 |

A is 4-hydroxy-2,2,6,6-tetramethyl-piperidinyl-1-oxy radical
E is N,N-bis-(1,4-dimethylpentyl)-1,4-phenylenediamine in combination with stearic acid (Molar Ratio 1:1.5)

EXAMPLES 16 to 21

The procedure of Examples 1 to 3 were repeated but a molar equivalent quantity of capric/caprylic acid was used in place of the stearic acid without any significant difference in results.

EXAMPLES 22 to 24

The procedures of Examples 4 to 6 were repeated but a molar equivalent quantity of capric/caprylic acid was used in place of the stearic acid without any significant difference in results.

EXAMPLES 25 to 27

The procedures of Examples 7 to 9 were repeated.

| Example No | Inhibitors | ppm | Polymer (ppm) |
|---|---|---|---|
| 25 | F | 10 | 414 |
| 26 | B | 150 | 19,970 |
| 27 | F plus B | 5 plus 75 | 397 |

B is 3,5-ditertiarybutyl-4-oxy-N,N-dimethylbenzylamine in combination with stearic acid (Molar Ratio 1:1.5)
F is ditertiary butyl nitroxide.

What is claimed is:

1. A monomer composition, stabilised against premature polymerisation, comprising:
    a) an ethylenically unsaturated monomer or mixture of monomers polymerisable by free radical initiation, and
    b) an effective amount, sufficient to inhibit premature polymerisation of component (a) of a mixture of:
        i) 1 to 99% by weight, based on the total weight of components (i) and (ii) of a mixture of at least one aromatic amine and at least one organic acid in a molar ratio of 10:1 to 1:10, and
        ii) 99 to 1% by weight based on the total weight of components (i) and (ii) of at least one stable radical compound, wherein the aromatic amine is selected from the group consisting of 3,5-ditertiarybutyl-4-oxy, N,N-dimethylbenzlamine; 1,4-phenylenediamine; and N,N'-bis-(1,4dimethylpentyl)-1,4-phenylenediamine; wherein the organic acid is a carboxylic acid; and wherein the stable radical compound is a sterically hindered nitroxyl selected from 1-oxyl-2,2,6,6-tetramethylpiperidin-4-ol, 1-oxyl 2,2,6,6-tetramethylpiperidin-4-one, 1-oxyl-2,2,6,6-tetramethylpiperidin-4-yl acetate, 1-oxyl 2,2,6,6-tetramethylpiperidin-4-yl sterate, 1-oxyl-2,2,6,6-tetramethylpiperidin-4-yl benzoate, 1-oxyl 2,2,6,6-tetramethylpiperidin-4-yl 4-tert-butykbenzoate, bis(1-oxyl-2,2,6,6-tetramethylpiperidin-4-yl) succinate, bis(1-oxyl-2,2,6,6-tetramethylpiperidin-4yl) sebacate, bis(1-oxyl-2,2,6,6-tetramethylpiperidin-4-yl benzoate) adipate, bis(1-oxyl-2,2,6,6-tetramethylpiperidin-4-yl) n-butylmalonate, bis(1-oxyl-2,2,6,6-tetramethylpiperidin-4-yl) phthalate, bis(1-oxyl-2,2,6,6-tetramethylpiperidin-4-yl) isophthalate, bis(1-oxyl-2,2,6,6-tetramethylpiperidin-4-yl)terephthalate, bis(1-oxyl-2,2,6,6-tetramethylpiperidin-4-yl) hexahydoterephthalate, N,N'-bis(1-oxyl-2,2,6,6-tetramethylpiperidin-4-yl) adipamine, and N-(1-oxyl-2,2,6,6-tetramethylpiperidin-4-yl) caprolactam.

2. A composition as claimed in claim 1, wherein the weight of component (i) is 50 to 99% and the weight of component (ii) is 50 to 1%.

3. A composition as claimed in claim 2, wherein the weight of component (i) is 67 to 99% and the weight of component (ii) is 33 to 1%.

4. A composition as claimed in claim 1, wherein the molar ratio of the aromatic amine to organic acid is 3:1 to 1:3.

5. A composition as claimed in claim 1, wherein the organic acid is a $C_6$ to $C_{22}$ carboxylic acid.

6. A composition as claimed in claim 1, wherein the organic acid is a $C_6$ to $C_{10}$ carboxylic acid.

7. A process for inhibiting premature polymerisation of a vinyl aromatic or aliphatic compound during distillation, purification or storage, comprising the step of incorporating therein an effective amount, sufficient to prevent premature polymerisation during distillation, purification or storage of a mixture of i) 1 to 99% by weight, based on the total weight of components (i) and (ii), of an admixture of at least one aromatic amine and at least on organic acid in a molar ratio of from 10:1 to 1:10 and ii) 99 to 1% by weight, based on the total weight of components (i) and (ii), of at least one stable radical compound, wherein the aromatic amine is selected from the group consisting of 3,5-ditertiarybutyl-4-oxy, N,N-dimethylbenzylamine; 1,4-phenylenediamine; and N,N'-bis-(1,4dimethylpentyl)-1,4-phenylenediamine;

wherein the organic acid is a carboxylic acid; and wherein the stable radical compound is a sterically hindered nitroxyl selected from 1-oxyl-2,2,6,6-tetramethylpiperidin-4-ol, 1-oxyl2,2,6,6-tetramethylpiperidin-4-one, 1-oxyl-2,2,6,6-tetramethylpiperidin-4-yl acetate, 1-oxyl2,2,6,6-tetramethylpiperidin-4-yl stearate, 1-oxyl-2,2,6,6-tetramethylpiperidin-4-yl benzoate, 1-oxyl2,2,6,6-tetramethylpiperidin-4-yl 4tert-butylbenzoate, bis(1-oxyl-2,2,6,6-tetramethylpiperidin-4yl) succinate, bis(1-oxyl2,2,6,6-tetramethylpiperidin-4-yl) sebacate, bis(1-oxyl-2,2,6,6-tetramethylpiperidin-4-yl benzoate) adipate, bis(1-oxyl-2,2,6,6-tetramethylpiperidin-4-yl) n-butylmalonate, bis(1-oxyl-2,2,6,6-tetramethylpiperidin-4-yl) phthalate, bis (1-oxyl-2,2,6,6-tetramethylpiperidin-4-yl)isophthalate, bis (1-oxyl-2,2,6,6-tetramethylpiperidin-4-yl) terephthalate, bis(1-oxyl-2,2,6,6-tetramethylpiperidin-4-yl) hexahydoterephthalate, N,N'-bis(1-oxyl-2,2,6,6-tetramethylpiperidin-4-yl) adipamine, and N-(1-oxyl-2,2,6,6tetramethylpiperidin-4-yl) caprolactam.

* * * * *